US006958407B2

(12) United States Patent
Mori et al.

(10) Patent No.: US 6,958,407 B2
(45) Date of Patent: Oct. 25, 2005

(54) PROCESS FOR PRODUCING PHENYL ESTER, AND CATALYST

(75) Inventors: Yoshihiko Mori, Kuwana (JP); Takao Doi, Mie (JP); Tetsuo Asakawa, Yokkaichi (JP); Takanori Miyake, Yokkaichi (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 10/980,238

(22) Filed: Nov. 4, 2004

(65) Prior Publication Data

US 2005/0065363 A1 Mar. 24, 2005

Related U.S. Application Data

(62) Division of application No. 10/292,439, filed on Nov. 13, 2002, now Pat. No. 6,815,394, and a division of application No. 09/670,268, filed on Sep. 27, 2000, now Pat. No. 6,528,679.

(30) Foreign Application Priority Data

Sep. 29, 1999 (JP) ................... 11-276632

(51) Int. Cl.[7] .......................... C07C 57/00; B01J 23/44; B01J 23/64
(52) U.S. Cl. ...................... 554/135; 502/325; 502/326; 502/327; 502/332; 502/333; 502/339; 554/134; 554/162; 560/131; 562/408
(58) Field of Search ............................... 502/325–327, 502/332, 333, 339; 554/134, 135, 162; 560/131; 562/408

(56) References Cited

U.S. PATENT DOCUMENTS

| 4,621,071 A | 11/1986 | Blanchard et al. .......... 502/302 |
| 5,208,204 A | 5/1993 | Subramanian et al. ...... 502/303 |
| 5,789,339 A | 8/1998 | Ziebarth et al. ............. 502/525 |
| 6,342,620 B1 * | 1/2002 | Mori .......................... 554/134 |
| 6,528,679 B1 | 3/2003 | Mori et al. ................. 560/254 |

FOREIGN PATENT DOCUMENTS

| JP | A-S46-33024 | 9/1971 | |
| JP | A-S48-4439 | 1/1973 | |
| JP | A-S48-18219 | 6/1973 | ........... C07C 39/04 |
| JP | A-S50-34544 | 11/1975 | ........... C07C 69/14 |
| JP | A-S52-27089 | 3/1977 | ............ B01J 31/04 |
| JP | A-S52-77892 | 6/1977 | ............ B01J 23/64 |
| JP | A-S52-130494 | 11/1977 | ............ B01J 23/64 |
| JP | A-S55-15455 | 4/1980 | ......... C07C 69/157 |
| JP | A-S56-21463 | 5/1981 | ............ B01J 23/64 |
| JP | A-S63-174950 | 7/1988 | ........... C07C 67/35 |
| JP | 01301644 | 12/1989 | |
| JP | 01301645 | 12/1989 | |
| JP | A-H2-13653 | 4/1990 | ........... C07C 67/17 |

* cited by examiner

*Primary Examiner*—Stanley S. Silverman
*Assistant Examiner*—Jonas N. Strickland
(74) *Attorney, Agent, or Firm*—Jeffrey I. Auerbach; Berenato, White & Stavish, LLC

(57) ABSTRACT

A phenyl ester is produced by allowing benzene, a carboxylic acid and molecular oxygen to react with each other in the presence of a catalyst comprising (A) palladium, (B) at least one element selected from elements of groups 13, 14, 15, and 16 and the fourth to sixth periods of the periodic table, and (C) at least one element selected from elements of groups 3, 4 and lanthanoid elements of the periodic table. Preferably, element (B) is selected from elements of group 16 and the fourth to sixth periods of the periodic table, and element (C) is contained in a metal oxide form in the catalyst. The catalytic activity can be maintained at a high level, and a phenyl ester is stably produced. The phenyl ester can be converted to phenol by a conventional procedure.

12 Claims, No Drawings

PROCESS FOR PRODUCING PHENYL ESTER, AND CATALYST

CROSS-REFERENCE TO RELATED APPLICATIONS

This application is a divisional application of U.S. patent application Ser. No. 10/292,439 (which application was filed on Nov. 13, 2002, and issued on Nov. 9, 2004 as U.S. Pat. No. 6,815,394), and of U.S. patent application Ser. No. 09/670,268 (which application was filed on Sep. 27, 2000, and issued on Mar. 4, 2003 as U.S. Pat. No. 6,528,679), both of which applications are herein incorporated by reference.

BACKGROUND OF THE INVENTION (1) Field of the Invention

This invention relates to a process for producing a phenyl ester in a high yield and stably by allowing benzene, a carboxylic acid and a molecular oxygen to react with each other in the presence of a specific palladium catalyst. It also relates to the specific palladium catalyst used in the process for the production of a phenyl ester.

(2) Description of the Related Art

A process for producing a phenyl ester by allowing benzene, a carboxylic acid and molecular oxygen to react with each other in the presence of a catalyst is well known. Proposals have been made wherein the reaction is conducted in the vapor phase or liquid phase using a noble metal catalyst. Palladium is most popularly used as the main ingredient of the noble catalyst, and some proposals also have been made wherein a co-catalyst comprising a metal, which exhibits by itself no catalytic activity for the specified reaction, is used in combination with the noble catalyst.

As examples of the process using a metal catalyst, there can be mentioned a process using at least one metal selected from palladium and platinum, described in Japanese Examined Patent Publication (hereinafter abbreviated to "JP-B") S46-33024, a process using a combination of at least one metal selected from palladium and platinum with elemental bismuth or tellurium, described in JP-B S48-18219. Further, a process using a catalyst comprising a combination of palladium or a palladium compound with at least one compound comprising a metal selected from cadmium, zinc, uranium, tin, lead, antimony, bismuth, tellurium and thallium, and in the presence of nitric acid is described in JP-B S55-15455.

A catalyst system comprising palladium and antimony, and an alkali metal salt as an activation promoter is described in JP-B 56-21463, Japanese Unexamined Patent Publication (hereinafter abbreviated to "JP-A") S52-27089, JP-A 552-77892 and JP-A S52-130494.

Further, as examples of the process using a metal compound as catalyst, there can be mentioned a process using a catalyst comprising a combination of at least one metal compound selected form an oxide, a hydroxide, an acetate or a nitrate of a metal selected from platinum, palladium, rhodium, ruthenium, iridium or osmium, with at least one alkali metal nitrate (JP-B S50-34544), a process using a combination of (a) at least one member selected from metallic palladium and palladium compounds, with (b) at least one compound selected from nitric acid, nitrous acid and metal salts of these acids, or a combination of (a), (b) with (c) at least one metal salt of a carboxylic acid (JP-A S48-4439, and a process using a combination of palladium acetate with antimony acetate, and at least one metal acetate, the metal of which is selected from chromium, nickel, manganese and iron (JP-B H2-13653).

The processes for allowing benzene, a carboxylic acid and molecular oxygen to react with each other in the liquid phase using a palladium catalyst or a palladium compound catalyst to produce a phenyl ester have a problem such that palladium metal is dissolved in the raw material liquid, and the catalytic activity is reduced with time. Palladium is expensive and thus the above processes are costly. If a step of recovering palladium is conducted, the production processes become complicated. Further, the operation of compensating the decrease of catalytic activity with time is troublesome and not advantageous from an industrial point of view.

In a process using a metal salt catalyst soluble in a reaction liquid, a step of recovering the metal salt must be conducted. Further, a problem arises such that, for example, a palladium salt is used, palladium metal is liable to be deposited on the inner wall of a reactor during the reaction, and this also leads to reduction of catalytic activity with time and loss of palladium.

A process comprising a liquid phase reaction using as a catalyst a combination of palladium with bismuth and/or lead wherein a soluble bismuth compound and/or a soluble lead compound is additionally incorporated in the reaction system is described in JP-A S63-174950. In this process, the soluble bismuth compound and/or the soluble lead compound prevents dissolution of metallic bismuth or lead supported on the palladium catalyst, and thus, dissolution of the main catalyst ingredient, i.e., palladium can be suppressed and the reduction with time of catalytic activity can be minimized. This process has a problem such that the amount of the soluble bismuth compound and/or the soluble lead compound incorporated is large, and the soluble compounds must be recovered as a crystal at the step of separating and purifying a phenyl ester, which leads to complication of the production process.

SUMMARY OF THE INVENTION

In view of the foregoing prior art, an object of the invention is to provide a process for producing a phenyl ester by allowing benzene, a carboxylic acid and molecular oxygen to react with each other in the presence of a palladium catalyst to produce a phenyl ester, whereby a high catalytic activity is maintained and a phenyl ester can be produced under stable conditions.

In accordance with the present invention, there is provided a process for producing a phenyl ester which comprises the step of:

allowing benzene, a carboxylic acid and molecular oxygen to react with each other in the presence of a catalyst comprising:

(A) palladium, (B) at least one element selected from the group consisting of elements of groups 13, 14, 15, and 16 and the fourth to sixth periods of the periodic table, and (C) at least one element selected from the group consisting of elements of groups 3, 4 and lanthanoid elements of the periodic table.

DETAILED DESCRIPTION OF THE PREFERRED EMBODIMENTS

Palladium (A) and element (B), which is at least one member selected from elements of groups 13, 14, 15, and 16 and the fourth to sixth periods of the periodic table, are used preferably in a metallic state. Palladium (A) and element (B)

selected from groups 13, 14, 15, and 16 and the fourth to sixth periods of the periodic table may form together an intermetallic compound.

Element (B) is not particularly limited provided that it is selected from groups 13, 14, 15, and 16 and the fourth to sixth periods of the periodic table. Usually element (B) is selected from those belonging to the fourth to sixth periods. Of these, lead, bismuth, antimony and tellurium are preferable. Among the elements of groups 13, 14, 15, and 16 and the fourth to sixth periods, those of group 16 are preferable. The ratio of element (B) to palladium is usually in the range of 0.01/1 to 20/1 by mol, preferably 0.02/1 to 2/1 by mol. When the ratio of element (B)/Pd is too small or too large, the effect of the invention becomes difficult to obtain.

Element (C), which is at least one element selected from the group consisting of elements of groups 3, 4 and lanthanoid elements of the periodic table, is preferably used in a metal oxide form. A part of element (C) may be in a metal form. Element (C) may form an intermetallic compound together with at least one of palladium (A) and element (B).

When the catalyst of the invention is supported on a carrier which is inactive to the reaction, element (C) selected from groups 3, 4 and lanthanoid elements of the periodic table may form a double oxide together with the carrier. When the catalyst of the invention is used without being supported on a carrier which is inactive to the reaction, at least one of palladium (A) and element (B) may be used in a form of being supported on a metal oxide comprising element (C), i.e., at least one element selected from groups 3, 4 and lanthanoid elements of the periodic table.

Element (C) is not particularly limited provided that it is selected from groups 3, 4 and lanthanoid elements of the periodic table. Usually element (C) is selected from those belonging to the fourth to sixth periods. Of these, yttrium, lanthanoid elements, titanium, zirconium and hafnium are preferable. Cerium, praseodymium, neodymium, titanium, zirconium and hafnium are especially preferable. The amount of element (C) is usually in the range of 0.1% to 99.99% by weight, preferably 1% to 99% by weight, based on the total weight of the catalyst. If the relative amount of element (C) is too small, the effect of the invention is difficult to obtain. In contrast, if the relative amount of element (C) is too large, the relative amount of the main catalyst ingredient, i.e., palladium, is reduced and the effect of the invention also is difficult to obtain.

The raw material for palladium (A) used is not particularly limited, and includes palladium metal and palladium compounds such as, for example, ammonium hexachloropalladate, potassium hexachloropalladate, sodium hexachloropalladate, ammonium tetrachloropalladate, potassium tetrachloropalladate, sodium tetrachloropalladate, potassium tetrabromopalladate, palladium oxide, palladium chloride, palladium bromide, palladium iodide, palladium nitrate, palladium sulfate, palladium acetate, potassium dinitrosulfite-palladate, chlorocarbonyl palladium, dinitrodiamminepalladium, tetraamminepalladium chloride, tetraamminepalladium nitrate, cis-diamminedichloropalladium, trans-diamminedichloro-palladium, dichloro(ethylenediamine)palladium, potassium tetracyanopalladate and acetylacetonatopalladium.

The raw material for element (B) is not particularly limited provided that it contains an element selected from groups 13, 14, 15, and 16 and the fourth to sixth periods of the periodic table. As specific examples of the raw material for element (B), there can be mentioned metallic lead and lead compounds such as lead acetate, lead chloride, lead fluoride, lead iodide, lead nitrate, lead oxide, lead sulfate, lead oxalate, lead naphthenate and lead stearate; metallic bismuth and bismuth compounds such as bismuth chloride, bismuth nitrate, bismuth oxychlorlde, bismuth acetate and bismuth oxide; metallic antimony and antimony compounds such as antimony fluoride, antimony chloride, antimony bromide, antimony iodide, antimony acetate, antimony methoxide, antimony ethoxide, antimony isopropoxide, antimony butoxide, antimony ethylene glycoxide, antimony potassium tartrate, antimony oxide, antimony sulfide, and complex compounds with an organic acid such as tartaric acid or oxalic acid; and metallic tellurium and tellurium compounds such as tellurium chloride, tellurium oxide, tellurium iodide and telluric acid.

The raw material for element (C) is not particularly limited provided that it contains an element selected from groups 3, 4 and lanthanoid elements of the periodic table. As specific examples of the raw material for element (C), there can be mentioned metallic cerium and cerium compounds such as cerium fluoride, cerium chloride, cerium bromide, cerium iodide, cerium acetate, cerium nitrate, ammonium cerium nitrate, diammonium cerium nitrate, cerium oxide, cerium sulfate, ammonium cerium sulfate, tetraammonium cerium sulfate, cerium carbonate, cerium oxalate and cerium acetylacetonate; metallic praseodymium and praseodymium compounds such as praseodymium acetate, praseodymium fluoride, praseodymium chloride, praseodymium nitrate, praseodymium oxide and praseodymium oxalate; metallic neodymium and neodymium compounds such as neodymium acetate, neodymium fluoride, neodymium chloride, neodymium nitrate, neodymium oxide, neodymium carbonate, neodymium oxalate and neodymium acetylacetonate; metallic titanium and titanium compounds such as titanium carbide, titanium chloride, titanium oxide, titanium sulfate, potassium titanium oxalate, titanium tetraethoxide, titanium tetraisopropoxide, titanium tetrabutoxide and titanium 2-ethyl-hexanolate; metallic zirconium and zirconium compounds such as zirconium chloride, zirconium oxychloride, zirconium oxide, zirconium oxynitrate, zirconium tetraisopropoxide, zirconium tetrabutoxide, zirconium acetylacetonate and zirconium naphthenate; and metallic hafnium and hafnium compounds such as hafnium chloride and hafnium oxide.

The amount of palladium (A) used is usually in the range of 0.01% to 10% by weight, preferably 0.1% to 5% by weight, based on the total weight of the catalyst. If the amount of palladium is smaller than 0.01% by weight, the rate of reaction is apt to be reduced. In contrast, if the amount of palladium is larger than 10%, the effect of the invention is not further enhanced and it is not advantageous from cost consideration.

The procedure by which the catalyst is prepared is not particularly limited. When the catalyst is supported on a carrier, a conventional procedure may be employed, which includes, for example, impregnation, ion exchange, precipitation and kneading procedures.

The carrier used for supporting the catalyst of the invention may be prepared by a conventional procedure. When the supported catalyst is prepared, a raw material for element (C) selected from groups 3, 4 and lanthanoid elements of the periodic table may be first combined with the carrier. For example, a co-precipitation procedure may be employed, in which a solution of a raw material for element (C) is treated with a precursor compound for the carrier whereby hydrolysis is caused to form a co-precipitate in the form of a double oxide. Then palladium (A) and element (B) selected from groups 13, 14, 15, and 16 and the fourth to sixth periods of the periodic table are supported on the double salt.

When a carrier which is inert itself to the intended reaction is not used, a raw material for element (C) selected from groups 3, 4 and lanthanoid elements of the periodic table may be first converted to a metal oxide by a conventional procedure, and then, palladium (A) and element (B) selected from groups 13, 14, 15, and 16 and the fourth to sixth periods of the periodic table may be supported on the metal oxide.

When the catalyst ingredients (A), (B) and (C) are supported on a carrier by an impregnation procedure, the carrier may be allowed to support either simultaneously these ingredients (A), (B) and (C), or, support first one of the ingredients (A), (B) and (C) and then the other ingredients.

According to the conventional impregnation or ion exchange procedure, the carrier having the as-supported catalyst is subjected to decantation, filtration, heating or vacuum-heating to remove the solvent used. Thereafter the catalyst-supported carrier is dried, for example, by heating or under a reduced pressure.

The dried catalyst supported on a carrier is subjected to a reduction treatment to activate the catalyst ingredient. Prior to the reduction treatment, the dried catalyst may be calcined. The calcination is carried out usually at a temperature of 200 to 700° C. in an oxygen-containing atmosphere such as oxygen, air or a mixture of oxygen with nitrogen, helium or argon.

The reduction treatment can be carried out by a conventional procedure. For example, a vapor phase reduction procedure using a reducing agent such as hydrogen, carbon monoxide, ethylene or methanol, or a liquid phase reduction procedure using a reducing agent such as hydrazine hydrate, formalin or formic acid. The vapor phase reduction treatment is carried out usually at a temperature of 100 to 700° C., preferably 100 to 600° C.

The carboxylic acid to be reacted with benzene and molecular oxygen includes those which have not larger than 10 carbon atoms. As specific examples of the carboxylic acid, there can be mentioned monocarboxylic acids such as acetic acid, propionic acid and butyric acid, and dioarboxylic acids such as adipic acid. Lower monocarboxylic acids having up to 6 carbon atoms such as acetic acid and propionic acid are preferable.

The amount of the carboxylic acid is not particularly limited, but is preferably in the range of 0.1 to 100 moles per mole of benzene.

The molecular oxygen used as an oxidizing agent in the process of the invention may be either pure oxygen or diluted with an inert gas such as nitrogen, helium or argon, and air may be used. The optimum amount of oxygen varies depending upon the reaction temperature, the amount of catalyst and other factors, and is not particularly limited provided that the gas composition flowing through a catalyst-packed bed is out of the explosive range.

Benzene, carboxylic acid and molecular oxygen are allowed to react with each other in the presence of the catalyst in the liquid phase, vapor phase or vapor-liquid mixed phase. The reaction apparatus is not particularly limited. For example, a fixed bed flow-through type reactor, a batch reactor and suspension bed reactor can be used.

The amount of the catalyst used varies depending upon the particular reaction procedure and is not particularly limited. For cost consideration, in the case where a fixed bed type reactor is used, the amount of the catalyst is usually in the range of 0.1 to 50 $h^{-1}$, preferably 0.1 to 30 $h^{-1}$, as liquid hourly space velocity (LHSV), i.e., as the total feed volume rate of benzene plus carboxylic acid per unit volume of the catalyst and per unit time (hr). In the case where a suspension bed type reactor is used, the concentration of the catalyst is preferably in the range of 0.05 to 30% by weight based on the total weight of benzene and carboxylic acid.

The reaction temperature is usually in the range of 100 to 300° C., preferably 100 to 250° C. The reaction pressure is normal pressure or higher, usually in the range of normal pressure to 200 atmospheric pressures, and preferably normal pressure to 100 atmospheric pressures.

The reaction time varies depending upon the reaction temperature and pressure, the amount of catalyst and the manner in which reaction is performed, and is not particularly limited. For example, when the reaction is performed in a batchwise or semi-batchwise manner, the reaction time is usually at least 0.5 hour. When the reaction is performed in continuous manner using a suspension bed or a fixed bed, the residence time is usually in the range of 0.03 to 10 hours.

Phenol can be easily produced from the phenyl ester obtained by the process of the invention. The procedure for producing phenol may be conventional and the reaction occurring for the production of phenol includes, for example, hydrolysis reaction and ester exchange reaction.

According to the process of the invention, the catalyst activity can be maintained at a high level, and a phenyl ester which is useful as a raw material for phenol can be stably produced.

The invention will now be described by the following examples that by no means limit the scope of the invention.

EXAMPLE 1

Preparation of Catalyst

In distilled water, 1.3 g of zirconyl nitrate was dissolved to obtain 21 ml of a zirconyl nitrate solution. To this solution, 20 g of silica ("CARIACT Q-30"™ supplied by Fuji Silysia Chemical Ltd.) was added whereby the silica was impregnated with the zirconyl nitrate solution. Then the solution-impregnated silica was dried under a reduced pressure and further dried at 110° C. overnight, and then calcined at 350° C. for 5 hours in air to prepare zirconia-supported silica.

In an eggplant type flask, 2.1 g of an aqueous nitric acid solution containing 8.4% by weight of palladium dinitrodiammine and 0.03 g of telluric acid were weighed, and then distilled water was added so that the total volume reached 6 ml. To this solution, 5.4 g of the previously prepared zirconia-supported silica was added whereby the zirconia-supported silica was impregnated with the palladium- and tellurium-containing solution. Then the impregnated zirconia-supported silica was dried under a reduced pressure and further dried at 110° C. overnight, then calcined at 600° C. for 5 hours in air. The calcined product was subjected to a reduction treatment with hydrogen at 150° C. for 16 hours to prepare a catalyst.

Synthesis of Phenyl Ester

A reaction tube having an inner diameter of 13 mm made of SUS 316 was packed with 10 ml of the above-prepared catalyst. An equimolar mixed liquid of benzene and acetic acid was continuously supplied into the reaction tube at a rate of 2.2 g/min together with 27 Nml/min of oxygen gas and 183 Nml/min of nitrogen at a catalyst layer temperature of 190° C. and a reaction pressure of 20 atmospheric pressures to carry out a reaction.

Samples of the reaction mixture were collected for analysis twice, i.e., 100 hours and 400 hours after the commencement of reaction. Each sample was separated into the gaseous component and the liquid component. The two components were analyzed by gas chromatography to determine the space-time-yield (hereinafter abbreviated to "STY") (in g/liter.hour) of phenyl acetate ester. The ratio of STY of phenyl acetate as measured on a sample collected 400 hours after the commencement of reaction (which STY is hereinafter referred to as "$STY_{400hr}$") to STY of phenyl acetate as measured on a sample collected 100 hours after the commencement of reaction (which STY is hereinafter referred to as "$STY_{100hr}$") was 0.99. The larger the ratio of $STY_{400hr}/STY_{100hr}$, the smaller the reduction of catalytic activity with time.

EXAMPLE 2

Preparation of Catalyst

In 500 ml of methanol, 5 g of zirconium tetraisopropoxide and 25 g of tetramethoxysilane were dissolved. To the thus-obtained solution, 50 ml of distilled water was gradually dropwise added with stirring. The mixture was ripened for 24 hours with stirring and then filtered. The precipitate thus-collected by filtration was placed in 500 ml of distilled water, and stirred for 10 minutes, and then filtered. This procedure for washing with water was repeated three times in total, and thereafter the water-washed precipitate was dried at 110° C. overnight and then calcined at 500° C. for 5 hours in air to prepare zirconia-silica double oxide.

In an eggplant type flask, 2.1 g of an aqueous nitric acid solution containing 8.4% by weight of palladium dinitrodiammine and 0.03 g of telluric acid were weighed, and then distilled water was added so that the total volume reached 6 ml. To this solution, 5.4 g of the previously prepared zirconia-silica double oxide was added whereby the double oxide was impregnated with the palladium- and tellurium-containing solution. Then the impregnated zirconia-silica double oxide was dried under a reduced pressure and further vacuum-dried at 100° C. for 3 hours, then calcined at 400° C. for 5 hours in air. The calcined product was subjected to a reduction treatment with hydrogen at 400° C. for 5 hours to prepare a catalyst. The catalyst was molded into a columnar tablet having a diameter of 4 mm and a height of 3 mm.

Synthesis of Phenyl Ester

A synthesis reaction was carried out by the same procedure as described in Example 1. The ratio of $STY_{400hr}/STY_{100hr}$ was 0.90.

EXAMPLE 3

Preparation of Catalyst

In 1,000 ml of distilled water, 50 g of zirconyl nitrate was dissolved. To the obtained zirconyl nitrate solution, 40 ml of aqueous ammonia with a concentration of 25% by weight was gradually dropwise added with stirring. After the completion of addition of aqueous ammonia, the solution exhibited a pH value of 9. Thereafter the solution was ripened for 24 hours with stirring, and then filtered. The precipitate thus-collected by filtration was placed in 500 ml of distilled water, and stirred for 10 minutes, and then filtered. This procedure for washing with water was repeated three times in total, and thereafter the water-washed precipitate was dried at 110° C. overnight to prepare zirconia.

In an eggplant type flask, 7.27 g of an aqueous solution containing 8.26% by weight of palladium nitrate was weighed, and 0.13 g of telluric acid was added and further distilled water was added so that the total volume reached 21 ml. To this aqueous solution, 20 g of the previously prepared zirconia was added whereby the zirconia was impregnated with the palladium- and tellurium-containing solution. Then the impregnated zirconia was dried under a reduced pressure and further vacuum-dried at 100° C. for 3 hours, then calcined at 400° C. for 5 hours in air. The calcined product was subjected to a reduction treatment with hydrogen at 400° C. for 5 hours to prepare a catalyst. The catalyst was molded into a columnar tablet having a diameter of 4 mm and a height of 3 mm.

Synthesis of Phenyl Ester

A synthesis reaction was carried out by the same procedure as described in Example 1. The ratio of $STY_{400hr}/STY_{100hr}$ was 0.97.

EXAMPLE 4

Preparation of Catalyst

In distilled water, 1.5 g of cerium nitrate was dissolved to obtain 21 ml of a cerium nitrate solution. To this solution, 20 g of silica ("CARIACT Q-30"™ supplied by Fuji Silysia Chemical Ltd.) was added whereby the silica was impregnated with the cerium nitrate solution. Then the solution-impregnated silica was dried under a reduced pressure and further dried at 110° C. overnight, and then calcined at 400° C. for 5 hours in air to prepare cerium oxide-supported silica.

In an eggplant type flask, 2.1 g of an aqueous nitric acid solution containing 8.4% by weight of palladium dinitrodiammine and 0.03 g of telluric acid were weighed, and then distilled water was added so that the total volume reached 6 ml. To this solution, 5.4 g of the previously prepared cerium oxide-supported silica was added whereby the cerium oxide-supported silica was impregnated with the palladium- and tellurium-containing solution. Then the impregnated cerium oxide-supported silica was dried under a reduced pressure and further dried at 110° C. overnight, then calcined at 600° C. for 5 hours in air. The calcined product was subjected to a reduction treatment with hydrogen at 400° C. for 5 hours to prepare a catalyst.

Synthesis of Phenyl Ester

A synthesis reaction was carried out by the same procedure as described in Example 1. The ratio of $STY_{400hr}/STY_{100hr}$ was 0.95.

EXAMPLE 5

Preparation of Catalyst

In Isopropanol, 2.1 g of tetraisopropoxytitanium was dissolved to obtain 21 ml of a titanium-containing solution. To this solution, 20 g of silica ("CARIACT Q-30"™ supplied by Fuji Silysia Chemical Ltd.) was added whereby the silica was impregnated with the titanium-containing solution. Then the solution-impregnated silica was dried under a reduced pressure and further dried at 110° C. overnight, and then calcined at 400° C. for 5 hours in air to prepare titania-supported silica.

In an eggplant type flask, 2.1 g of an aqueous nitric acid solution containing 8.4% by weight of palladium dinitrodiammine and 0.03 g of telluric acid were weighed, and then distilled water was added so that the total volume reached 6 ml. To this solution, 5.4 g of the previously prepared titania-supported silica was added whereby the titania-supported silica was impregnated with the palladium- and tellurium-containing solution. Then the impregnated titania-supported silica was dried under a reduced pressure and further dried at 110° C. overnight, then calcined at 450° C. for 5 hours in air. The calcined product was subjected to a reduction treatment with hydrogen at 400° C. for 5 hours to prepare a catalyst.

Synthesis of Phenyl Ester

A synthesis reaction was carried out by the same procedure as described in Example 1. The ratio of $STY_{400hr}/STY_{100hr}$ was 0.90.

EXAMPLE 6

Preparation of Catalyst

In distilled water, 1.5 g of praseodymium nitrate was dissolved to obtain 21 ml of a praseodymium-containing solution. To this solution, 20 g of silica ("CARIACT Q-30"™ supplied by Fuji Silysia Chemical Ltd.) was added whereby the silica was impregnated with the praseodymium-containing solution. Then the solution-impregnated silica was dried under a reduced pressure and further dried at 110° C. overnight, and then calcined at 400° C. for 5 hours in air to prepare praseodymium oxide-supported silica.

In an eggplant type flask, 2.1 g of an aqueous nitric acid solution containing 8.4% by weight of palladium dinitrodiammine and 0.03 g of telluric acid were weighed, and then distilled water was added so that the total volume reached 6 ml. To this solution, 5.4 g of the previously prepared prasebdymium oxide-supported silica was added whereby the praseodymium oxide-supported silica was impregnated with the palladium- and tellurium-containing solution. Then the impregnated praseodymium oxide-supported silica was dried under a reduced pressure and further dried at 110° C. overnight, then calcined at 600° C. for 5 hours in air. The calcined product was subjected to a reduction treatment with hydrogen at 400° C. for 5 hours to prepare a catalyst.

Synthesis of Phenyl Ester

A synthesis reaction was carried out by the same procedure as described in Example 1. The ratio of $STY_{400hr}/STY_{100hr}$ was 0.96.

Comparative Example 1

A catalyst was prepared by the same procedure as described in Example 1 except that zirconia was not supported on silica. Using the catalyst, a phenyl ester was synthesized by the same procedure as described in Example 1. The ratio of $STY_{400hr}/STY_{100hr}$ was 0.51.

EXAMPLE 7

Preparation of Catalyst

In distilled water, 11.3 g of tartaric acid was dissolved, and then 1.6 g of antimony oxide was dissolved in the solution while being warmed. Thereafter 4.6 g of zirconyl nitrate was dissolved to obtain 50 ml of a zirconium-containing solution. To this solution, 50 g of silica ("CARIACT Q-30"™ supplied by Fuji Silysia Chemical Ltd.) was added whereby the silica was impregnated with the antimony- and zirconium-containing solution. Then the solution-impregnated silica was dried under a reduced pressure and further dried at 110° C. overnight, and then calcined at 500° C. for 5 hours in air to prepare antimony oxide/zirconia-supported silica.

In an eggplant type flask, 5.6 g of an aqueous nitric acid solution containing 8.4% by weight of palladium dinitrodiammine and 0.1 g of telluric acid were weighed, and then distilled water was added so that the total volume reached 15 ml. To this solution, 15 g of the previously prepared antimony oxide/zirconia-supported silica was added whereby the antimony oxide/zirconia-supported silica was impregnated with the palladium- and tellurium-containing solution. Then the impregnated antimony oxide/zirconia-supported silica was dried under a reduced pressure and further dried at 110° C. overnight, then calcined at 500° C. for 5 hours in air. The calcined product was subjected to a reduction treatment with hydrogen at 50° C. for 5 hours to prepare a catalyst.

Synthesis of Phenyl Ester

A synthesis reaction was carried out by the same procedure as described in Example 1. The ratio of $STY_{400hr}/STY_{100hr}$ was 0.86.

Comparative Example 2

Preparation of Catalyst

In 2.7 ml of distilled water, 0.6 g of tartaric acid was dissolved, and then 0.07 g of antimony oxide was dissolved in the solution while being warmed. Thereafter 2.1 g of an aqueous nitric acid solution containing 8.4% by weight of palladium dinitrodiammine and 0.03 g of telluric acid were added, and further distilled water was added so that the total volume reached 6 ml. To this solution, 5.4 g of silica ("CARIACT Q-30"™ supplied by Fuji Silysia Chemical Ltd.) was added whereby the silica was impregnated with the antimony/palladium/tellurium-containing solution. Then the impregnated silica was dried under a reduced pressure, vacuum-dried at 100° C. for 3 hours, and further dried at 100° C. overnight. Then the dried product was calcined at 400° C. for 5 hours in air, and then subjected to a reduction treatment with hydrogen at 400° C. for 5 hours to prepare a catalyst.

Synthesis of Phenyl Ester

A synthesis reaction was carried out by the same procedure as described in Example 1. The ratio of $STY_{400hr}/STY_{100hr}$ was 0.60.

EXAMPLE 8

Preparation of Catalyst

In an eggplant type flask, 32 g of an aqueous nitric acid solution containing 8.4% by weight of palladium dinitrodiammine and 0.5 g of telluric acid were weighed. Then 80 g of zirconia ("XZ 16052"™ supplied by Saint-Gobain-Norton Co.) was added whereby the zirconia was impregnated with the palladium- and tellurium-containing solution. Then the impregnated zirconia was dried under a reduced pressure and further dried at 110° C. overnight, then calcined at 500° C. for 5 hours in air. The calcined product was subjected to a reduction treatment with hydrogen at 400° C. for 5 hours to prepare a catalyst.

Synthesis of Phenyl Ester

A reaction tube having an inner diameter of 13 mm made of SUS 316 was packed with 10 ml of the above-prepared catalyst. An equimolar mixed liquid of benzene and acetic acid was continuously supplied into the reaction tube at a rate of 2.2 g/min together with 34 Nml/min of oxygen gas and 176 Nml/min of nitrogen at a catalyst layer temperature of 190° C. and a reaction pressure of 40 atmospheric pressures to carry out a synthesis reaction.

Samples of the reaction mixture were collected for analysis three times, i.e., 5 hours, 100 hours and 400 hours after the commencement of reaction. Analysis of the samples by gas chromatography revealed that STYs of phenyl acetate, i.e., $STY_{5hr}$, $STY_{100hr}$ and $STY_{400hr}$, were 300 g/liter.hour, 205 g/liter.hour, and 190 g/liter.hour, respectively. The ratio of $STY_{400hr}/STY_{100hr}$ was 0.93.

Comparative Example 3

A catalyst was prepared by the same procedure as described in Example 1 except that zirconia was not used. Using the catalyst, a phenyl ester was synthesized by the same procedure as described in Example 8. Yields of phenyl acetate ($STY_{100hr}$ and $STY_{400hr}$) as measured 100 hours and 400 hours after the commencement of reaction were 73 g/liter.hour and 40 g/liter.hour, respectively. The ratio of $STY_{400hr}/STY_{100hr}$ was 0.55.

Comparative Example 4

A catalyst was prepared by the same procedure as described in Example 1 except that telluric acid was not used. Using the catalyst, a phenyl ester was synthesized by the same procedure as described in Example 8. Yield of phenyl acetate as measured 3 hours after the commencement of reaction was 83 g/liter.hour. But, STY of phenyl acetate as measured 24 hours after the commencement of reaction was 4 g/liter.hour. When 50 hours elapsed from the commencement of reaction, the reaction did not occur to any appreciable extent.

What is claimed is:

1. A process for producing phenol which comprises the steps of: allowing benzene, a carboxylic acid and molecular oxygen to react with each other in the presence of a catalyst comprising:
   (A) palladium,
   (B) at least one element selected from the group consisting of elements of the fourth to sixth periods of groups 13, 14, 15 and 16 of the periodic table, and
   (C) at least one element selected from the group consisting of elements of groups 3, 4 and lanthanoid elements of the periodic table to give a phenyl ester; and then, subjecting the phenyl ester to hydrolysis or ester exchange; wherein the palladium (a) and the at least one element (b) are each in a metallic state.

2. The process for producing phenol according to claim 1, wherein said element (C) is contained in the form of a metal oxide in the catalyst.

3. The process for producing phenol according to claim 1, wherein the palladium (A), the element (B), and the element (C) are supported on a carrier.

4. The process for producing phenol according to claim 1, wherein the element (B) is selected from elements of group 16 of the periodic table.

5. The process for producing phenol according to claim 1, wherein the element (B) is selected from the group consisting of lead, bismuth, antimony, and tellurium.

6. The process for producing phenol according to claim 1, wherein the element (C) is selected from the group consisting of cerium, praseodymium, neodymium, titanium, zirconium and hafnium.

7. The process for producing phenol according to claim 1, wherein the element (B) is selected from the group consisting of antimony and tellurium.

8. The process for producing phenol according to claim 1, wherein the element (C) is selected from the group consisting of cerium, praseodymium, titanium, and zirconium.

9. The process for producing phenol according to claim 1, wherein the element (B) is selected from the fourth to sixth periods of group 13 of the periodic table.

10. The process for producing phenol according to claim 1, wherein the element (B) is selected from the fourth to sixth periods of group 15 of the periodic table.

11. The process for producing phenol according to claim 1, wherein the catalyst has been subjected to a reduction treatment.

12. The process for producing phenol according to claim 1, wherein a phenyl ester is produced by allowing benzene, a carboxylic acid, and molecular oxygen to react with each other in the presence of the catalyst.

* * * * *